(12) United States Patent
Whitehurst et al.

(10) Patent No.: US 8,600,512 B2
(45) Date of Patent: Dec. 3, 2013

(54) METHODS AND SYSTEMS FOR TREATING SEIZURES CAUSED BY BRAIN STIMULATION

(75) Inventors: Todd K. Whitehurst, Santa Clarita, CA (US); Rafael Carbunaru, Valley Village, CA (US); Kristen N. Jaax, Santa Clarita, CA (US); Andrew DiGiore, Santa Monica, CA (US); Brett Schleicher, Valencia, CA (US); Greg Baldwin, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1097 days.

(21) Appl. No.: 12/339,639

(22) Filed: Dec. 19, 2008

(65) Prior Publication Data

US 2009/0192568 A1  Jul. 30, 2009

Related U.S. Application Data

(60) Provisional application No. 61/016,642, filed on Dec. 26, 2007.

(51) Int. Cl.
*A61N 1/00* (2006.01)
(52) U.S. Cl.
USPC .................................. 607/45; 607/3
(58) Field of Classification Search
USPC .................................. 607/2, 3, 45
See application file for complete search history.

(56) References Cited

U.S. PATENT DOCUMENTS

| | | | |
|---|---|---|---|
| 5,193,539 A | 3/1993 | Schulman et al. | |
| 5,193,540 A | 3/1993 | Schulman et al. | |
| 5,312,439 A | 5/1994 | Loeb | |
| 5,501,703 A | 3/1996 | Holsheimer et al. | |
| 5,938,688 A | 8/1999 | Schiff | |
| 5,995,868 A * | 11/1999 | Dorfmeister et al. | 600/544 |
| 6,016,449 A | 1/2000 | Fischell et al. | |
| 6,051,017 A | 4/2000 | Loeb et al. | |
| 6,134,474 A | 10/2000 | Fischell et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,230,049 B1 | 5/2001 | Fischell et al. | |
| 6,280,873 B1 | 8/2001 | Tsukamoto | |
| 6,341,236 B1 | 1/2002 | Osorio et al. | |
| 6,354,299 B1 | 3/2002 | Fischell et al. | |
| 6,360,122 B1 | 3/2002 | Fischell et al. | |
| 6,381,496 B1 | 4/2002 | Meadows et al. | |
| 6,458,171 B1 | 10/2002 | Tsukamoto | |
| 6,463,328 B1 | 10/2002 | John | |

(Continued)

FOREIGN PATENT DOCUMENTS

| | | |
|---|---|---|
| WO | WO 01/28622 A2 | 4/2001 |
| WO | WO 2005/030025 A2 | 4/2005 |

(Continued)

*Primary Examiner* — Scott Getzow
(74) *Attorney, Agent, or Firm* — Vista IP Law Group LLP

(57) ABSTRACT

Methods for treating seizures caused by brain stimulation include providing a stimulator, programming the stimulator with one or more stimulation parameters configured to treat a medical condition, applying at least one stimulus with the stimulator to a stimulation site within the brain of a patient in accordance with the one or more stimulation parameters, and monitoring the patient for a seizure caused by the at least one stimulus.

9 Claims, 10 Drawing Sheets

(56) References Cited

U.S. PATENT DOCUMENTS

| | | |
|---|---|---|
| 6,487,446 B1 | 11/2002 | Hill et al. |
| 6,516,227 B1 | 2/2003 | Meadows et al. |
| 6,539,263 B1 | 3/2003 | Schiff et al. |
| 6,553,263 B1 | 4/2003 | Meadows et al. |
| 6,587,727 B2 | 7/2003 | Osorio et al. |
| 6,596,439 B1 | 7/2003 | Tsukamoto et al. |
| 6,605,383 B1 | 8/2003 | Wu |
| 6,607,843 B2 | 8/2003 | Ruth, II et al. |
| 6,647,296 B2 | 11/2003 | Fischell et al. |
| 6,671,556 B2 | 12/2003 | Osorio et al. |
| 6,760,626 B1 | 7/2004 | Boveja |
| 6,882,881 B1 | 4/2005 | Lesser et al. |
| 6,920,357 B2 | 7/2005 | Osorio et al. |
| 6,961,618 B2 | 11/2005 | Osorio et al. |
| 7,193,539 B2 | 3/2007 | Kim et al. |
| 7,457,665 B1 | 11/2008 | Osorio et al. |
| 7,501,703 B2 | 3/2009 | Minervini |
| 2001/0051819 A1 | 12/2001 | Fischell et al. |
| 2002/0072776 A1 | 6/2002 | Osorio et al. |
| 2002/0072782 A1 | 6/2002 | Osorio et al. |
| 2002/0099412 A1 | 7/2002 | Fischell et al. |
| 2002/0169485 A1 | 11/2002 | Pless et al. |
| 2003/0074032 A1* | 4/2003 | Gliner .................. 607/45 |
| 2003/0195574 A1 | 10/2003 | Osorio et al. |
| 2004/0138721 A1 | 7/2004 | Osorio et al. |
| 2004/0220644 A1 | 11/2004 | Shalev et al. |
| 2005/0021104 A1* | 1/2005 | DiLorenzo .................. 607/45 |
| 2005/0149123 A1 | 7/2005 | Lesser et al. |
| 2005/0182288 A1 | 8/2005 | Zabara |
| 2005/0228461 A1 | 10/2005 | Osorio et al. |
| 2006/0212093 A1 | 9/2006 | Pless et al. |
| 2007/0043402 A1 | 2/2007 | Echauz et al. |
| 2007/0142874 A1 | 6/2007 | John |
| 2007/0265664 A1 | 11/2007 | Gerber et al. |
| 2008/0269542 A1 | 10/2008 | Zabara |

FOREIGN PATENT DOCUMENTS

| | | |
|---|---|---|
| WO | WO 2005/065768 A1 | 7/2005 |
| WO | WO 2007/024702 A2 | 3/2007 |
| WO | WO 2007/127460 A2 | 11/2007 |
| WO | WO 2008/070001 A2 | 6/2008 |

* cited by examiner

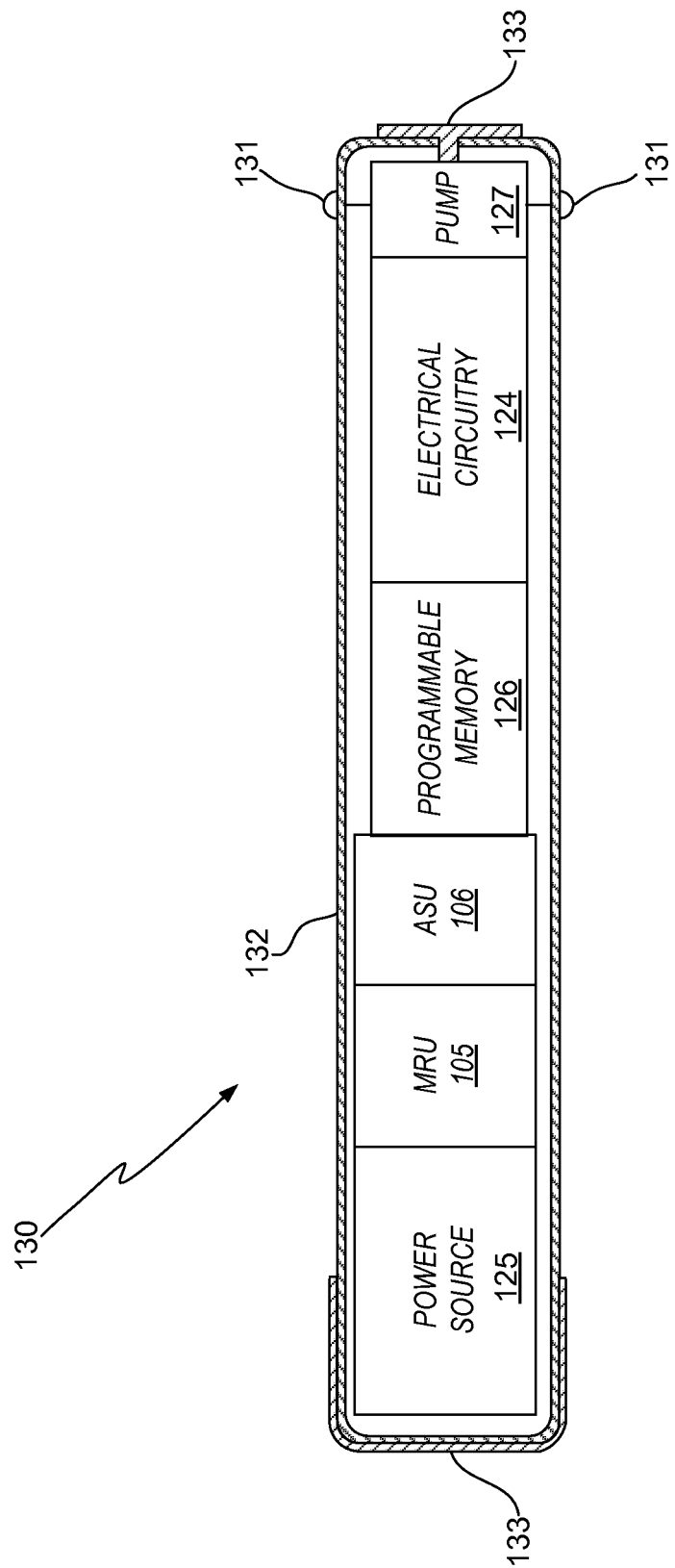

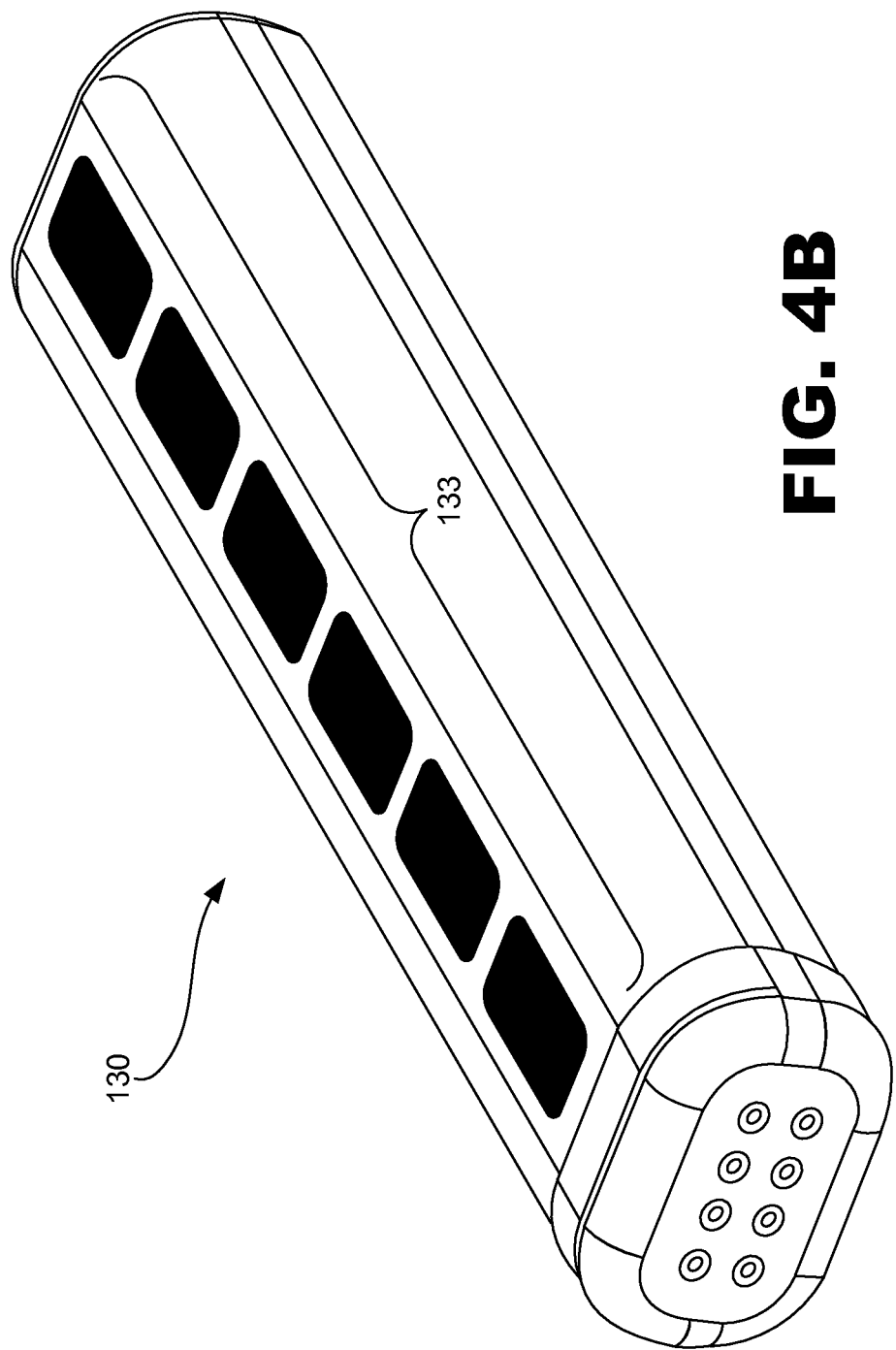

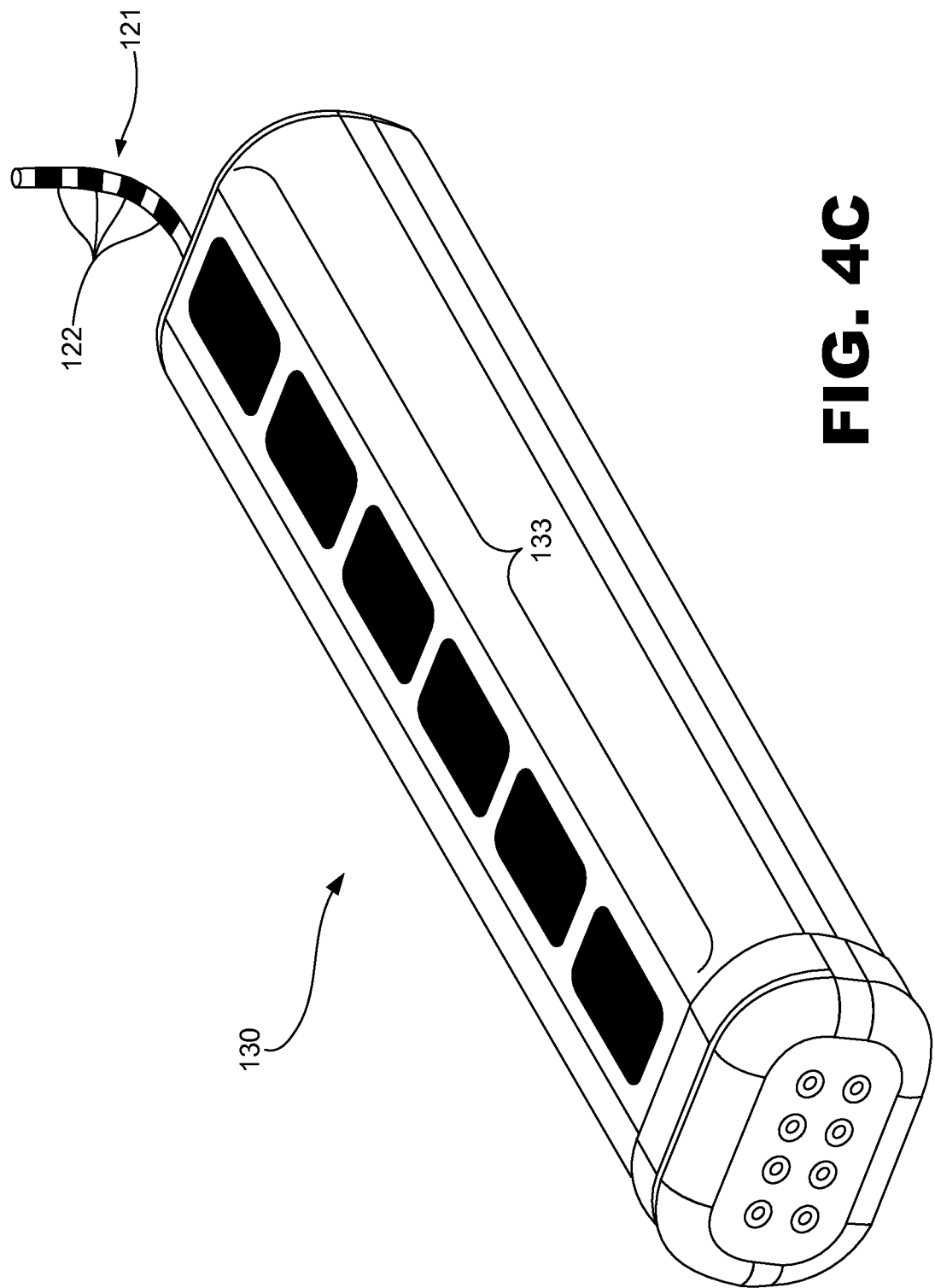

METHODS AND SYSTEMS FOR TREATING SEIZURES CAUSED BY BRAIN STIMULATION

RELATED APPLICATIONS

The present application claims priority under 35 U.S.C. §119(e) to U.S. Provisional Patent Application No. 61/016,642 by Todd K. Whitehurst et al., filed on Dec. 26, 2007, and entitled "METHODS AND SYSTEMS FOR TREATING SEIZURES CAUSED BY BRAIN STIMULATION," the contents of which are hereby incorporated by reference in their entirety.

BACKGROUND

Stimulation of the brain (e.g., deep brain stimulation) is often used to treat a variety of medical conditions including, but not limited to, Parkinson's disease, dystonia, essential tremor, epilepsy, obesity, depression, motor control disorders, and other debilitating diseases. To facilitate brain stimulation, a lead with one or more electrodes disposed thereon may be strategically placed at a stimulation site in the brain. Electrical stimulation generated by a stimulator may then be applied to the stimulation site via one or more of the electrodes.

While brain stimulation has proven to be quite effective in treating many different medical conditions, a number of negative side effects are often associated with the treatment. For example, brain stimulation may actually cause generalized seizures, which can be detrimental to a patient and his or her safety, health, and well-being.

SUMMARY

Methods of treating seizures caused by brain stimulation include providing a stimulator, programming the stimulator with one or more stimulation parameters configured to treat a medical condition, applying at least one stimulus with the stimulator to a stimulation site within the brain of a patient in accordance with the one or more stimulation parameters, and monitoring the patient for a seizure caused by the at least one stimulus.

Systems for treating seizures caused by brain stimulation include a stimulator configured to generate at least one stimulus in accordance with one or more stimulation parameters adjusted to treat a medical condition, a programmable memory unit in communication with the stimulator and programmed to store the one or more stimulation parameters to at least partially define the stimulus such that the stimulus is configured to treat the medical condition, means for applying the stimulus to a stimulation site within the brain of the patient, and a monitoring unit that is a part of the stimulator and configured to monitor the patient for a seizure caused by the at least one stimulus.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

FIG. 3 illustrates an exemplary microstimulator according to principles described herein.

FIG. 4B shows an example of a microstimulator with a plurality of electrodes disposed on an outer surface thereof according to principles described herein.

FIG. 4C shows the exemplary microstimulator of FIG. 4B coupled to a lead having a number of electrodes disposed thereon.

Throughout the drawings, identical reference numbers designate similar, but not necessarily identical, elements.

DETAILED DESCRIPTION

Methods and systems for treating seizures caused by brain stimulation are described herein. A stimulator may be provided that is configured to apply at least one stimulus to the brain of a patient in order to treat a particular medical condition. The stimulator may also be configured to monitor the patient for an event associated with an impending or already occurring seizure that may occur as a result of the stimulus being applied to the brain. If the stimulator detects any such seizure, the stimulator is configured to treat the seizure. As used herein, "treating" a seizure caused by brain stimulation refers to any action that prevents a seizure from occurring, stops an already occurring seizure, reduces the severity of a seizure, and/or warns the patient of an impending or already occurring seizure.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
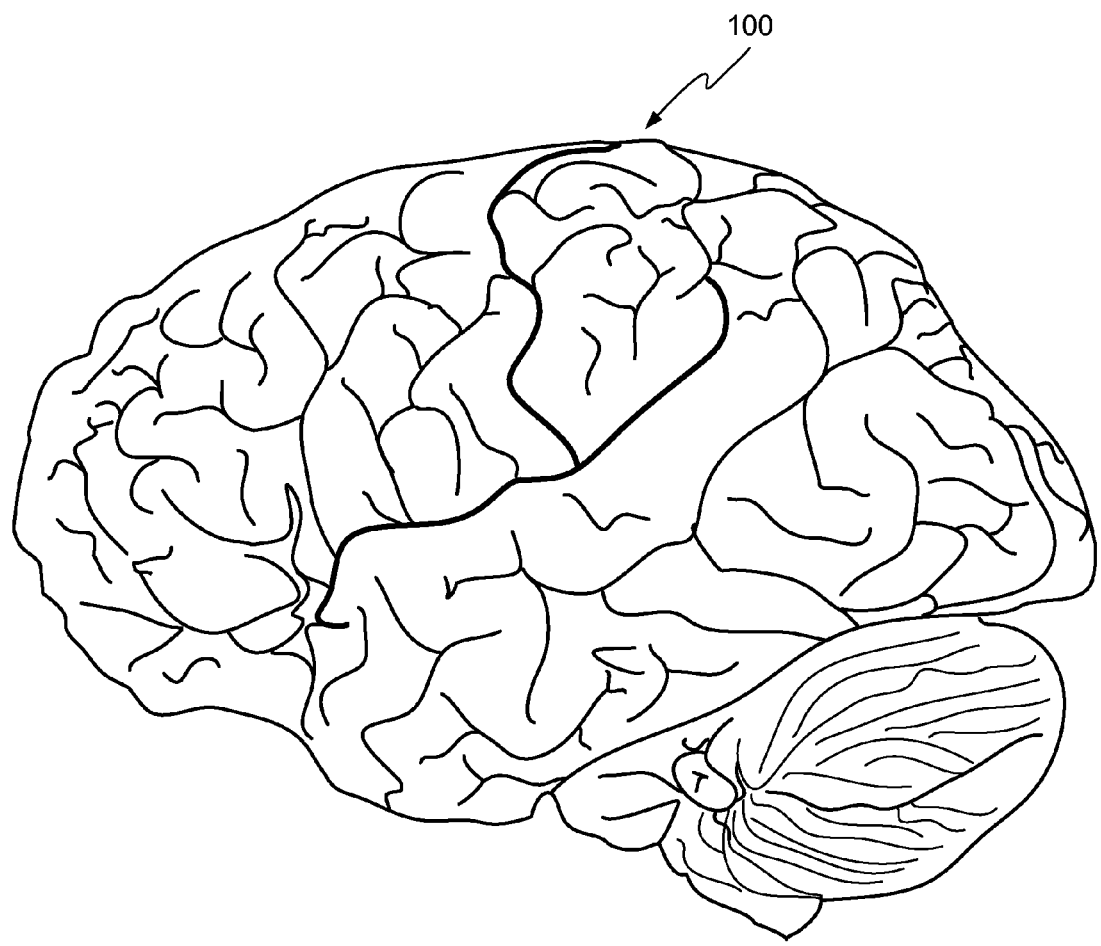
FIG. 1 depicts an exemplary human brain.

FIG. 1 depicts an exemplary human brain 100. As mentioned, one or more stimulation sites within the brain 100 are often stimulated in order to treat a variety of medical conditions. In some examples, the stimulation is provided by a stimulator, which may be implanted within the patient or located external to the patient. As used herein, and in the appended claims, the term "stimulator" will be used broadly to refer to any device configured to deliver a stimulus to a stimulation site within the brain. Thus, the term "stimulator" includes, but is not limited to, a deep brain stimulator, microstimulator, implantable pulse generator (IPG), spinal cord stimulator (SCS), external trial stimulator, system control unit, drug pump, or similar device.

Figure 2:
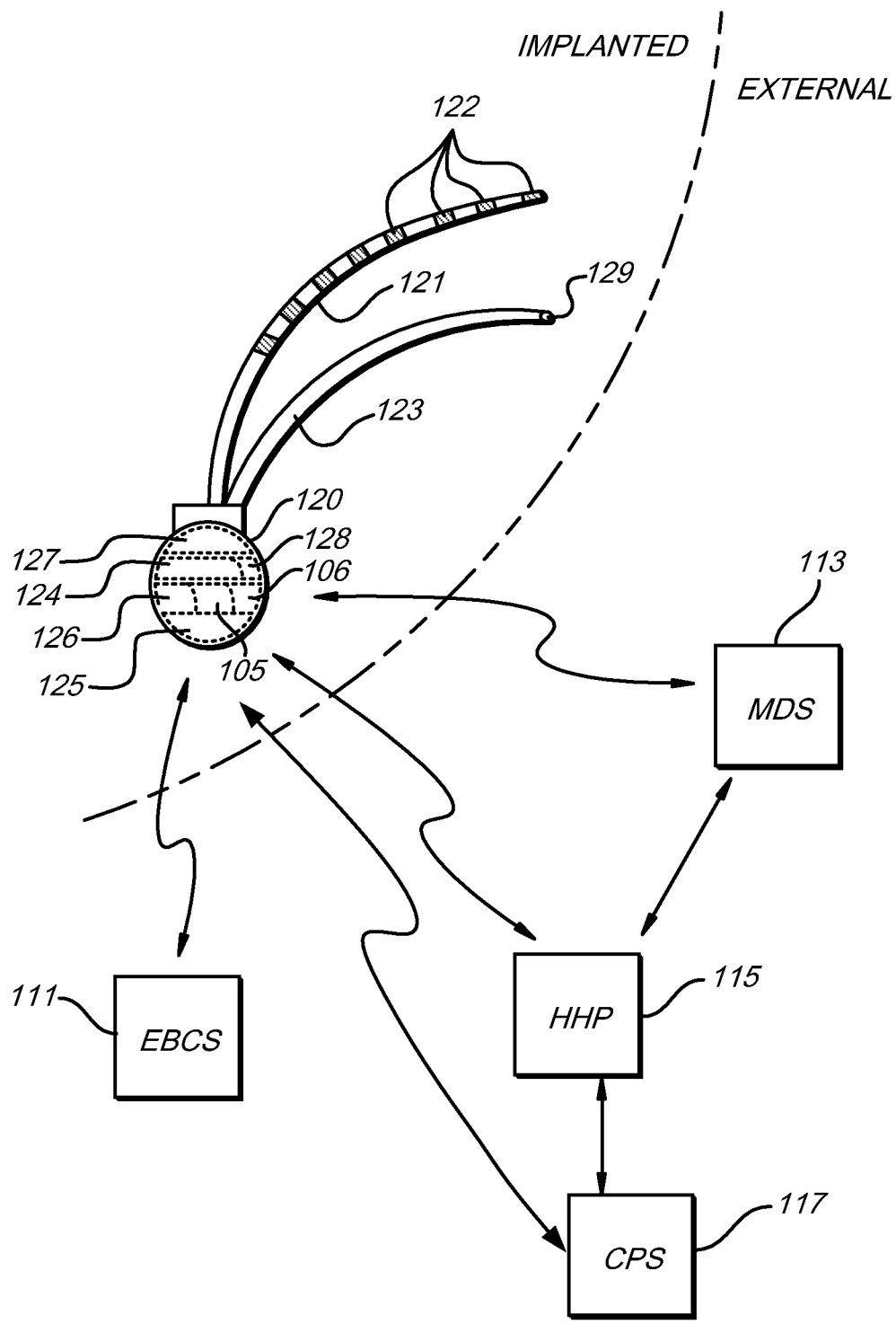
FIG. 2 illustrates an exemplary implantable stimulator according to principles described herein.

A more detailed description of an exemplary stimulator and its operation will now be given in connection with FIG. 2. FIG. 2 illustrates an exemplary stimulator 120 that may be used to apply a stimulus to a stimulation site within a patient, e.g., an electrical stimulation of the stimulation site, an infusion of one or more drugs at the stimulation site, or both. The electrical stimulation function of the stimulator 120 will be described first, followed by an explanation of the possible drug delivery function of the stimulator 120. It will be understood, however, that the stimulator 120 may be configured to provide only electrical stimulation, only drug stimulation, both types of stimulation, or any other type of stimulation as best suits a particular patient.

The exemplary stimulator 120 shown in FIG. 2 is configured to provide electrical stimulation to one or more stimulation sites within a patient and may include at least one lead 121 coupled thereto. In some examples, the at least one lead 121 includes a number of electrodes 122 through which electrical stimulation current may be applied by the stimulator 120 to a stimulation site. It will be recognized that the at least one lead 121 may include any number of electrodes 122 arranged in any configuration as best serves a particular application. In some alternative examples, as will be described in more detail below, the stimulator 120 is leadless.

As illustrated in FIG. 2, the stimulator 120 includes a number of components. It will be recognized that the stimulator 120 may include additional and/or alternative components as best serves a particular application. A power source 125 is configured to output voltage used to supply the various components within the stimulator 120 with power and/or to generate the power used for electrical stimulation. The power source 125 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), an osmotic pressure pump (where mechanical energy is generated due to fluid ingress), or the like.

In some examples, the power source 125 may be recharged using an external charging system. One type of rechargeable power supply that may be used is described in U.S. Pat. No. 6,596,439, which is incorporated herein by reference in its entirety. Other battery construction techniques that may be used to make the power source 125 include those shown, e.g., in U.S. Pat. Nos. 6,280,873; 6,458,171; 6,605,383; and 6,607,843, all of which are incorporated herein by reference in their respective entireties.

The stimulator 120 may also include a coil 128 configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 125.

For example, an external battery charging system (EBCS) 111 may be provided to generate power that is used to recharge the power source 125 via any suitable communication link. Additional external devices including, but not limited to, a hand held programmer (HHP) 115, a clinician programming system (CPS) 117, and/or a manufacturing and diagnostic system (MDS) 113 may also be provided and configured to activate, deactivate, program, and/or test the stimulator 120 via one or more communication links. It will be recognized that the communication links shown in FIG. 2 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 120. It will be recognized that any suitable communication link may be used among the various devices illustrated.

The external devices shown in FIG. 2 are merely illustrative of the many different external devices that may be used in connection with the stimulator 120. Furthermore, it will be recognized that the functions performed by any two or more of the external devices shown in FIG. 2 may be performed by a single external device.

The stimulator 120 may also include electrical circuitry 124 configured to generate the electrical stimulation current that is delivered to a stimulation site via one or more of the electrodes 122. For example, the electrical circuitry 124 may include one or more processors, capacitors, integrated circuits, resistors, coils, and/or any other component configured to generate electrical stimulation current.

Additionally, the exemplary stimulator 120 shown in FIG. 2 may be configured to provide drug stimulation to a patient by applying one or more drugs at a stimulation site within the patient. To this end, a pump 127 may also be included within the stimulator 120. The pump 127 is configured to store and dispense one or more drugs, for example, through a catheter 123. The catheter 123 is coupled at a proximal end to the stimulator 120 and may have an infusion outlet 129 for infusing dosages of the one or more drugs at the stimulation site and/or at any other site within the patient. In some embodiments, the stimulator 120 may include multiple catheters 123 and/or pumps 127 for storing and infusing dosages of the one or more drugs at the stimulation site.

The stimulator 120 may also include a programmable memory unit 126 configured to store one or more stimulation parameters. The stimulation parameters may include, but are not limited to, electrical stimulation parameters, drug stimulation parameters, and other types of stimulation parameters. The programmable memory unit 126 allows a patient, clinician, or other user of the stimulator 120 to adjust the stimulation parameters such that the stimulation applied by the stimulator 120 is safe and efficacious for treatment of a particular patient. The programmable memory unit 126 may include any type of memory unit such as, but not limited to, random access memory (RAM), static RAM (SRAM), a hard drive, or the like.

The electrical stimulation parameters may control various parameters of the stimulation current applied to a stimulation site including, but not limited to, the frequency, pulse width, amplitude, waveform (e.g., square or sinusoidal), electrode configuration (i.e., anode-cathode assignment), burst pattern (e.g., continuous or intermittent), duty cycle or burst repeat interval, ramp on time, and ramp off time. The drug stimulation parameters may control various parameters including, but not limited to, the amount of drugs infused at the stimulation site, the rate of drug infusion, and the frequency of drug infusion. For example, the drug stimulation parameters may cause the drug infusion rate to be intermittent, continuous, or bolus.

Specific stimulation parameters may have different effects on different medical conditions. Thus, in some examples, the stimulation parameters may be adjusted at any time throughout the treatment course as best serves the particular patient being treated. It will be recognized that any of the characteristics of the stimulation current, including, but not limited to, the pulse shape, amplitude, pulse width, frequency, burst pattern (e.g., continuous or intermittent), duty cycle or burst repeat interval, ramp on time, and ramp off time may be adjusted throughout the course of treatment as best serves a particular application.

In some examples, the stimulator 120 may also include a monitoring unit 105 configured to monitor the patient for one or more seizures that may be caused by the stimulation applied by the stimulator 120 to the brain. As will be described in more detail below, the monitoring unit 105 may be further configured to detect one or more events indicative of an impending seizure caused by the brain stimulation and/or an already occurring seizure being caused by the brain stimulation.

The monitoring unit 105 is communicatively coupled to the programmable memory unit 126 and/or any other component within the stimulator 120 so that data acquired by the monitoring unit 105 may be used to adjust the stimulation parameters used to generate the stimulation applied by the stimulator 120. The monitoring unit 105 may include any combination of hardware, software, and/or firmware as may serve a particular application.

In some examples, the stimulator 120 may also include an anti-seizure unit 106 configured to treat one or more seizures caused by the brain stimulation. Various methods of treating seizures caused by brain stimulation will be described in more detail below. The anti-seizure unit 106 may be communicatively coupled to the programmable memory unit 126, the monitoring unit 105, and/or any other component within the stimulator 120 as may serve a particular application. The anti-seizure unit 106 may include any combination of hardware, software, and/or firmware as may serve a particular application.

The stimulator 120 of FIG. 2 is illustrative of many types of stimulators that may be used in accordance with the systems and methods described herein. For example, the stimulator 120 may include a deep brain stimulator, an implantable pulse generator (IPG), a spinal cord stimulator (SCS), a drug pump, or any other type of implantable device configured to deliver a stimulus to a stimulation site within the brain of a patient. Exemplary deep brain stimulators suitable for use as described herein include, but are not limited to, those disclosed in U.S. Pat. Nos. 5,938,688; 6,016,449; and 6,539,263. Exemplary IPGs suitable for use as described herein include, but are not limited to, those disclosed in U.S. Pat. Nos. 6,381, 496, 6,553,263; and 6,760,626. Exemplary spinal cord stimulators suitable for use as described herein include, but are not limited to, those disclosed in U.S. Pat. Nos. 5,501,703; 6,487, 446; and 6,516,227. All of these listed patents are incorporated herein by reference in their respective entireties.

The stimulator 120 of FIG. 2 may alternatively include a microstimulator, such as a BION® microstimulator (Advanced Bionics® Corporation, Valencia, Calif.). Various details associated with the manufacture, operation, and use of implantable microstimulators are disclosed in U.S. Pat. Nos. 5,193,539; 5,193,540; 5,312,439; 6,185,452; 6,164,284; 6,208,894; and 6,051,017. All of these listed patents are incorporated herein by reference in their respective entireties.

FIG. 3 illustrates an exemplary microstimulator 130 that may be used as the stimulator 120 described herein. Other configurations of the microstimulator 130 are possible, as shown in the above-referenced patents and as described further below.

As shown in FIG. 3, the microstimulator 130 may include the power source 125, the programmable memory 126, the electrical circuitry 124, the pump 127, the monitoring unit 105, and the anti-seizure unit 106 described in connection with FIG. 2. These components are housed within a capsule 132. The capsule 132 may be a thin, elongated cylinder or any other shape as best serves a particular application. The shape of the capsule 132 may be determined by the structure of the desired stimulation site and the method of implantation. In some examples, the microstimulator 130 may include two or more leadless electrodes 133 disposed on the outer surface thereof.

The external surfaces of the microstimulator 130 may advantageously be composed of biocompatible materials. For example, the capsule 132 may be made of glass, ceramic, metal, or any other material that provides a hermetic package that will exclude water vapor but permit passage of electromagnetic fields used to transmit data and/or power. The electrodes 133 may be made of a noble or refractory metal or compound, such as platinum, iridium, tantalum, titanium, titanium nitride, niobium or alloys of any of these, in order to avoid corrosion or electrolysis which could damage the surrounding tissues and the device.

The microstimulator 130 may also include one or more infusion outlets 131 configured to dispense one or more drugs directly at a stimulation site. Alternatively, one or more catheters may be coupled to the infusion outlets 131 to deliver the drug therapy to a treatment site some distance from the body of the microstimulator 130.

Figure 4A:
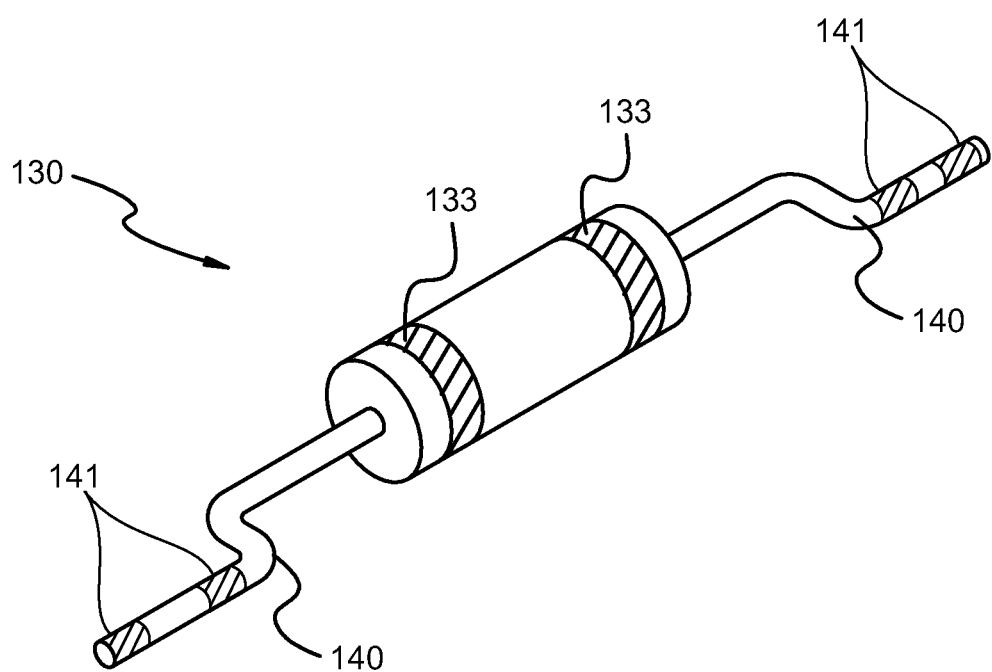
FIG. 4A shows an example of a microstimulator with one or more leads coupled thereto according to principles described herein.

FIGS. 4A-4C show alternative configurations of a microstimulator 130. It will be recognized that the alternative configurations shown in FIGS. 4A-4C are merely illustrative of the many possible configurations of a microstimulator 130. For example, FIG. 4A shows an example of a microstimulator 130 with one or more leads 140 coupled thereto. As shown in FIG. 4A, each of the leads 140 may include one or more electrodes 141 disposed thereon. The microstimulator 130 of FIG. 4A may additionally or alternatively include one or more leadless electrodes 133 disposed on the outer surface thereof.

FIG. 4B illustrates an exemplary microstimulator 130 with a plurality of electrodes 133 disposed on an outer surface thereof. In some examples, any number of electrodes 133 may be disposed on the outer surface of the microstimulator 130. In some alternative examples, as shown in FIG. 4C, the microstimulator 130 may be coupled to a lead 121 having a number of electrodes 122 disposed thereon. Each of the electrodes 133 and 122 may be selectively configured to serve as an anode or as a cathode.

Figure 5:
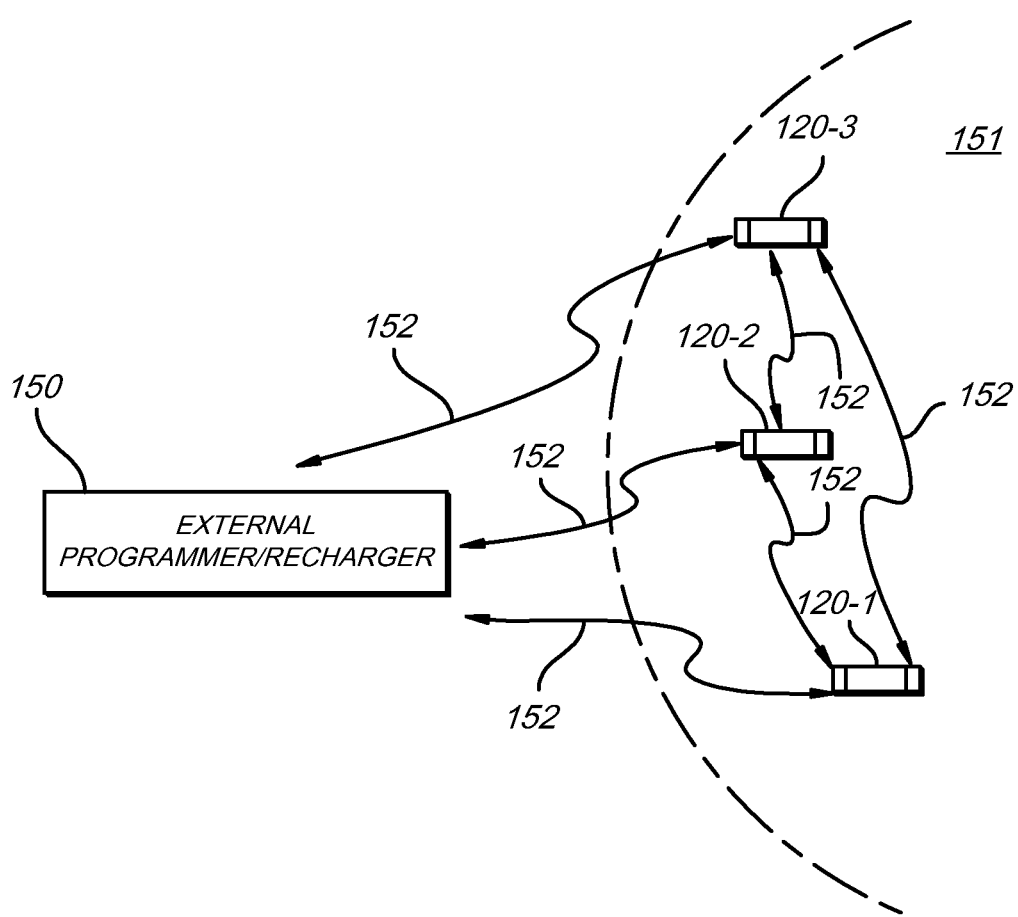
FIG. 5 depicts a number of stimulators configured to communicate with each other and/or with one or more external devices according to principles described herein.

In some examples, the stimulator 120 of FIG. 2 may be configured to operate independently. Alternatively, as shown in FIG. 5, the stimulator 120 may be configured to operate in a coordinated manner with one or more additional stimulators, other implanted devices, or other devices external to the patient's body. FIG. 5 illustrates an exemplary configuration wherein a first stimulator 120-1 implanted within the patient 151 provides a stimulus to a first location, a second stimulator 120-2 provides a stimulus to a second location, and a third stimulator 120-3 provides a stimulus to a third location. In some examples, one or more external devices 150 may be configured to control the operation of each of the implanted devices 120. In some embodiments, an implanted device, e.g., stimulator 120-1, may control, or operate under the control of, another implanted device(s), e.g., stimulator 120-2 and/or stimulator 120-3. Control lines 152 have been drawn in FIG. 5 to illustrate that the external device 150 may communicate or provide power to any of the implanted devices 120 and that each of the various implanted devices 120 may communicate with and, in some instances, control any of the other implanted devices.

As a further example of multiple stimulators 120 operating in a coordinated manner, the first and second stimulators 120-1 and 120-2 of FIG. 5 may be configured to sense various indicators of a medical condition being treated and transmit the measured information to the third stimulator 120-3. The third stimulator 120-3 may then use the measured information to adjust its stimulation parameters and apply stimulation to a stimulation site accordingly. The various implanted stimulators may, in any combination, sense indicators of the medical condition, communicate or receive data regarding such indicators, and adjust stimulation parameters accordingly.

In order to determine the strength and/or duration of electrical stimulation and/or amount and/or type(s) of stimulating drug(s) required to most effectively treat a particular medical condition, various indicators of the medical condition and/or a patient's response to treatment may be sensed or measured. The stimulator 120 may then adjust the stimulation parameters (e.g., in a closed loop manner) in response to one or more of the sensed indicators. Exemplary indicators include, but are not limited to, electrical activity of the brain (e.g., EEG), neurotransmitter levels, patient input, ocular motility test results, and/or other eye examination test results. In some examples, the stimulator 120 may be configured to perform one or more of the measurements. Alternatively, other sensing devices may be configured to perform the measurements and transmit the measured values to the stimulator 120.

Thus, one or more external devices may be provided to interact with the stimulator 120, and may be used to accomplish at least one or more of the following functions:

Function 1: If necessary, transmit electrical power to the stimulator 120 in order to power the stimulator 120 and/or recharge the power source 125.

Function 2: Transmit data to the stimulator 120 in order to change the stimulation parameters used by the stimulator 120.

Function 3: Receive data indicating the state of the stimulator 120 (e.g., battery level, drug level, stimulation parameters, etc.).

Additional functions may include adjusting the stimulation parameters based on information sensed by the stimulator 120 or by other sensing devices.

As mentioned, each of the stimulators described herein may be used to apply a stimulus to a stimulation site within the brain in order to treat one or more of a variety of medical conditions. However, during the course of treatment, the stimulus applied by a stimulator may cause the patient to experience one or more seizures. Additionally or alternatively, seizures may be a side effect of the implant procedure used to implant one or more stimulating devices (e.g., the stimulator, lead(s), and/or catheter(s)) within the patient.

Hence, in some examples, a stimulator 120 may be configured to detect and treat seizures caused by brain stimulation and/or the implantation of one or more stimulating devices. Various stimulator configurations for detecting a seizure caused by brain stimulation will first be described, followed by a discussion of various configurations that may be used to treat a detected seizure.

In some examples, the stimulator 120 may be configured to detect an onset of a seizure caused by brain stimulation before the seizure actually occurs. For example, electrical activity within a normally functioning brain can be measured as asynchronous brain waves that fluctuate slightly with no particular pattern. However, prior to an onset of a seizure caused by brain stimulation, these brain waves may become synchronous or include some other signature electric pulse.

To this end, the stimulator 120 may be configured to monitor brain waves by sensing electrical activity within the brain with one or more electrodes. The brain waves may be monitored during a stimulation therapy session or at any other time as may serve a particular application. Moreover, the stimulator 120 may be configured to monitor the brain waves continuously, intermittently, or on demand. When the stimulator 120 detects a brain wave indicative of an impending seizure (e.g., when the stimulator 120 detects synchronous brain waves), the stimulator 120 may be configured to perform an action configured to prevent, disrupt, or otherwise treat the impending seizure.

In some examples, one or more of the electrodes 122 described hereinabove may be configured to monitor brain waves by sensing electrical activity within the brain. Additionally or alternatively, one or more electrodes dedicated to sensing electrical activity of the brain may be coupled to the stimulator 120 and configured to sense electrical activity of the brain. As will be described in more detail below, the dedicated sensing electrodes may be disposed on a distinct lead 121.

In some examples, the sensing electrodes may be implanted at any suitable site within the brain. For example, the sensing electrodes may be implanted such that they are in communication with the cortex, the stimulation site being treated, or any other site within the brain. Additionally or alternatively, the sensing electrodes may be configured to be located externally and monitor brain waves transcutaneously.

Additionally or alternatively, the stimulator 120 may be configured to detect a seizure caused by brain stimulation by detecting a change in a concentration of one or more substances within the patient that have been shown to reveal the onset of seizures. These substances include, but are not limited to, glycogen, glucose, glutamate, aspartate, phosphocreatine, and potassium.

To this end, the stimulator 120 may include and/or be in communication with a sensor configured to detect changes in concentrations of substances that are indicative of an impending seizure. In some examples, if the stimulator 120 detects an increase in concentration of one or more of these substances above a programmable threshold, the stimulator may be configured to perform an action configured to prevent, disrupt, or otherwise treat the impending seizure. Additionally or alternatively, if the stimulator 120 detects a decrease in concentration of one or more of these substances below a programmable threshold, the stimulator 120 may be configured to perform an action configured to prevent, disrupt, or otherwise treat the impending seizure.

Additionally or alternatively, the stimulator 120 may be configured to detect a seizure caused by brain stimulation by detecting movement patterns of the patient that are associated with a seizure. Movement patterns associated with an impending seizure include, but are not limited to, spasms, sudden movements, and tremors. To this end, the stimulator 120 may include and/or be in communication with one or more accelerometers and/or other movement sensors. If the stimulator 120 detects a movement pattern indicative of an impending seizure, the stimulator 120 may be configured to perform an action configured to prevent, disrupt, or otherwise treat the impending seizure.

Additionally or alternatively, the stimulator 120 may be configured to detect a seizure caused by brain stimulation by monitoring patient input or feedback. In many instances, a patient can sense that he or she is about to experience a seizure as a result of brain stimulation. To this end, the patient may communicate to the stimulator 120 the presence of an impending seizure. Upon receiving this communication, the stimulator 120 may be configured to perform an action configured to prevent, disrupt, or otherwise treat the impending seizure. In some examples, the patient may communicate with the stimulator 120 via one or more programming devices, remote controls, or other external devices communicatively coupled to the stimulator 120.

As mentioned, once the stimulator 120 has detected a seizure caused by brain stimulation (which may be impending or actually occurring), the stimulator 120 may treat the seizure in a variety of different manners. For example, as will be described in more detail below, the stimulator 120 may prevent, stop, disrupt, reduce the severity of, and/or warn the patient of the seizure.

In some examples, the stimulator 120 may be configured to treat a sensed seizure by adjusting the stimulation parameters that control the stimulation being applied by the stimulator 120 to the brain. For example, the frequency, pulse width, amplitude, and/or any other characteristic of electrical stimulation being applied to the brain by the stimulator 120 may be adjusted in accordance with pre-programmed stimulation algorithms configured to treat seizures.

Additionally or alternatively, the stimulator 120 may be configured to switch from synchronous electrical stimulation to asynchronous electrical stimulation when a seizure is detected. It is believed that asynchronous electrical stimulation may be effective in disrupting the synchronous brain waves that are often associated with the occurrence of a seizure. Hence, application of asynchronous electrical stimulation by the stimulator 120 to the brain may be effective in treating a seizure caused by brain stimulation.

Additionally or alternatively, the stimulator 120 may be configured to stop applying stimulation to the brain when a seizure is detected. To this end, the stimulator 120 may include a switch or other shut-off mechanism configured to turn off stimulation being applied to the brain when the stimulator 120 detects a seizure. In some examples, the shut-off mechanism may be controlled by an external device operable by the patient. In this manner, the patient may invoke a command configured to activate the shut-off mechanism via the external device when the patient feels the onset of a seizure.

Additionally or alternatively, the stimulator 120 may be configured to treat a sensed seizure caused by brain stimulation by activating inhibitory pathways within the brain. For example, the stimulator 120 may be configured to infuse an inhibitory substance (e.g., GABA, dopamine, and/or other neurotransmitters) into the brain. It is believed that activation of inhibitory pathways within the brain may be useful in preventing, disrupting or otherwise alleviating a seizure caused by brain stimulation.

In some examples, the stimulator 120 may additionally or alternatively be configured to warn a patient of a seizure caused by brain stimulation via an alarm. The alarm may be a part of an external device worn or otherwise accessed by the user. For example, the alarm may be included within a remote control, external programming device, pager, mobile telephone, personal computer, or any other external device configured to be communicatively coupled to the stimulator 120. The alarm may include an audio signal, a vibration, a visual display, and/or any other feature configured to alert the patient of the presence of a seizure. The stimulator 120 may be configured to communicate with the alarm using any suitable communication link as described hereinabove in connection with FIG. 2.

Figure 6:
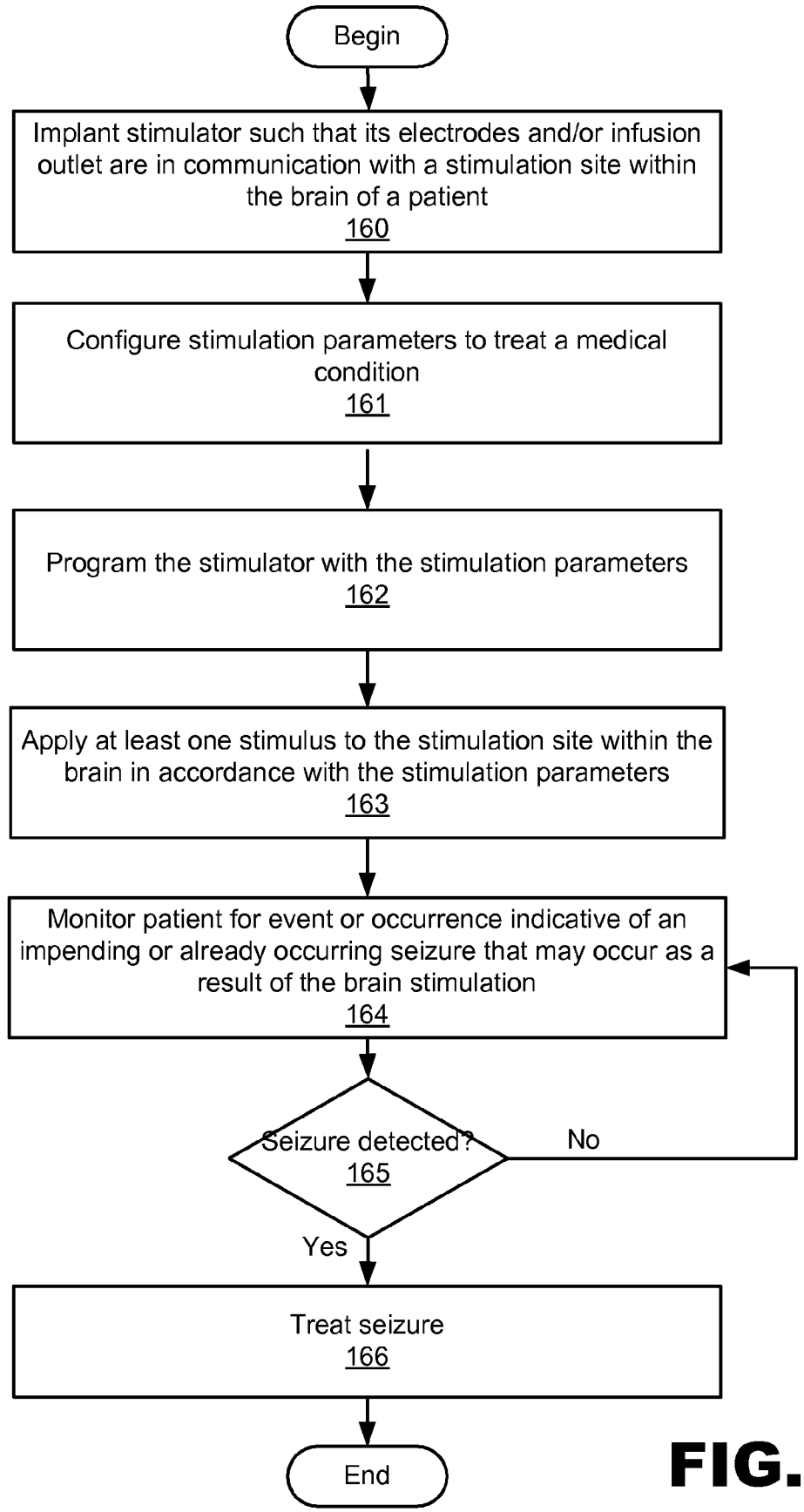
FIG. 6 is a flow chart illustrating an exemplary method of treating a seizure caused by brain stimulation according to principles described herein.

By way of example, an exemplary method of treating a seizure caused by brain stimulation may be carried out according to the steps shown in the flow chart of FIG. 6. The steps shown in FIG. 6 may be modified, reordered, and/or added to as may serve a particular application.

In step 160, a stimulator 120 is implanted so that its electrodes and/or infusion outlet are in communication with a stimulation site within the brain of a patient. As used herein and in the appended claims, the term "in communication with" refers to the stimulator, stimulating electrodes, and/or infusion outlet being adjacent to, in the general vicinity of, in close proximity to, directly next to, or directly on the stimulation site. In some alternative examples, the stimulator is located external to the patient.

In step 161, one or more stimulation parameters are configured to treat a medical condition. The stimulator may then be programmed with the one or more stimulation parameters configured to treat the medical condition, as shown in step 162. The stimulator may then generate and apply at least one stimulus to the stimulation site within the brain in accordance with the stimulation parameters, as shown in step 163. The stimulus may include electrical stimulation, drug stimulation, gene infusion, chemical stimulation, thermal stimulation, electromagnetic stimulation, mechanical stimulation, and/or any other suitable stimulation.

During the course of the brain stimulation treatment, the stimulator monitors the patient for any event or occurrence indicative of an impending or already occurring seizure that may occur as a result of the brain stimulation (step 164). For example, the stimulator may be configured to sense one or more brain waves indicative of a seizure, detect a change in concentration of one or more substances indicative of a seizure, detect movement patterns indicative of a seizure, and/or monitor patient feedback indicative of a seizure.

If a seizure is detected by the stimulator, the stimulator treats the seizure, as shown in step 166. The seizure may be treated by adjusting the stimulation parameters, applying an asynchronous electrical stimulation pulse to one or more locations within the brain, stopping the stimulation, activating inhibitory pathways within the brain, warning the patient of the seizure, and/or performing any other function as may serve a particular application.

The stimulator may be implanted within a patient using any suitable surgical procedure such as, but not limited to, small incision, open placement, laparoscopy, or endoscopy. Exemplary methods of implanting a deep brain stimulator, for example, are described in U.S. Pat. Nos. 7,938,688; 6,016,449; and 6,539,263. Exemplary methods of implanting a microstimulator, for example, are described in U.S. Pat. Nos. 7,193,539; 5,193,540; 5,312,439; 6,185,452; 6,164,284; 6,208,894; and 6,051,017. Exemplary methods of implanting an SCS, for example, are described in U.S. Pat. Nos. 7,501,703; 6,487,446; and 6,516,227. All of these listed patents are incorporated herein by reference in their respective entireties.

Figure 7:
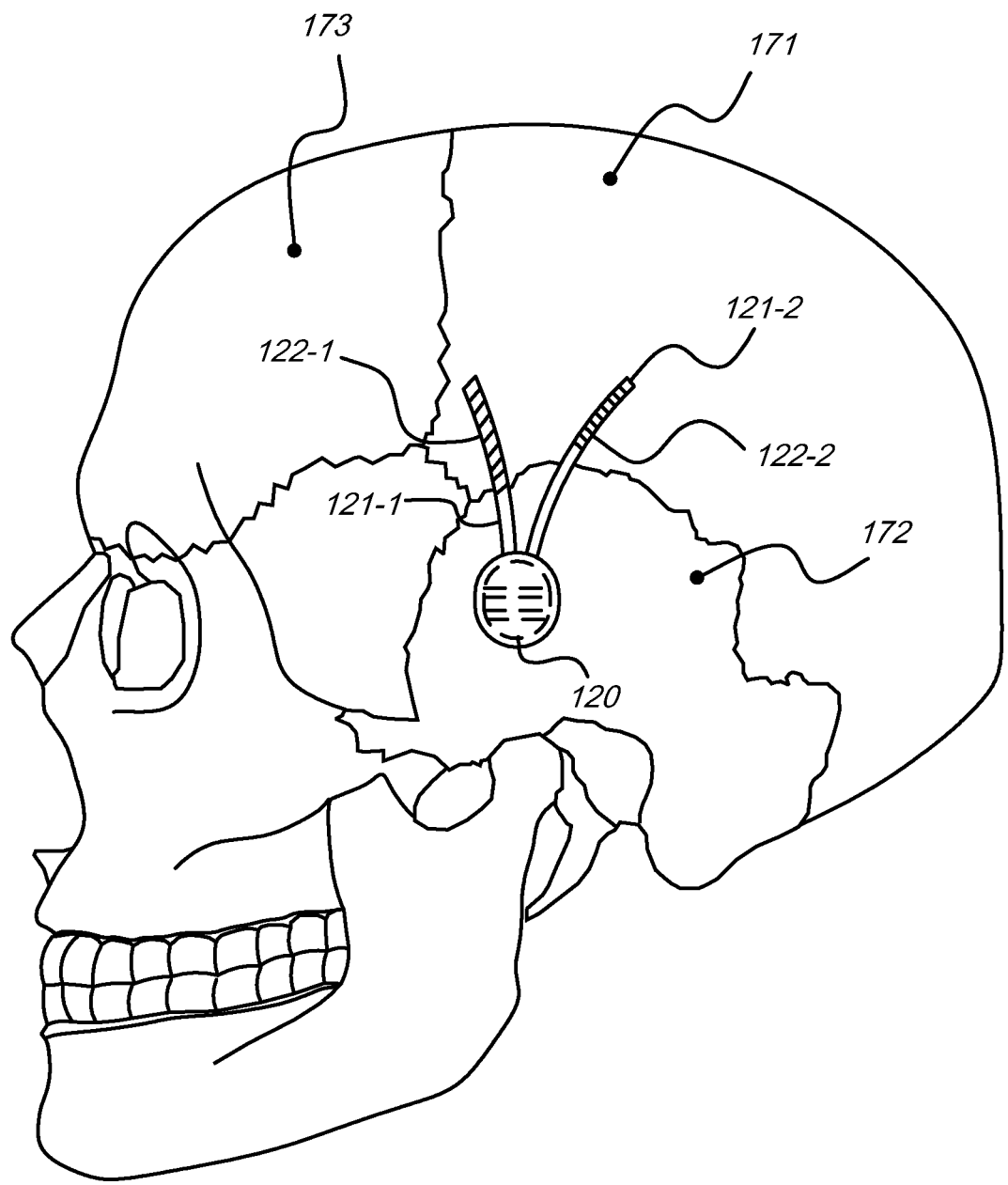
FIGS. 7-8 illustrate exemplary configurations wherein one or more electrodes coupled to an implantable stimulator are in communication with one or more stimulation sites within the brain of a patient according to principles described herein.
Figure 8:
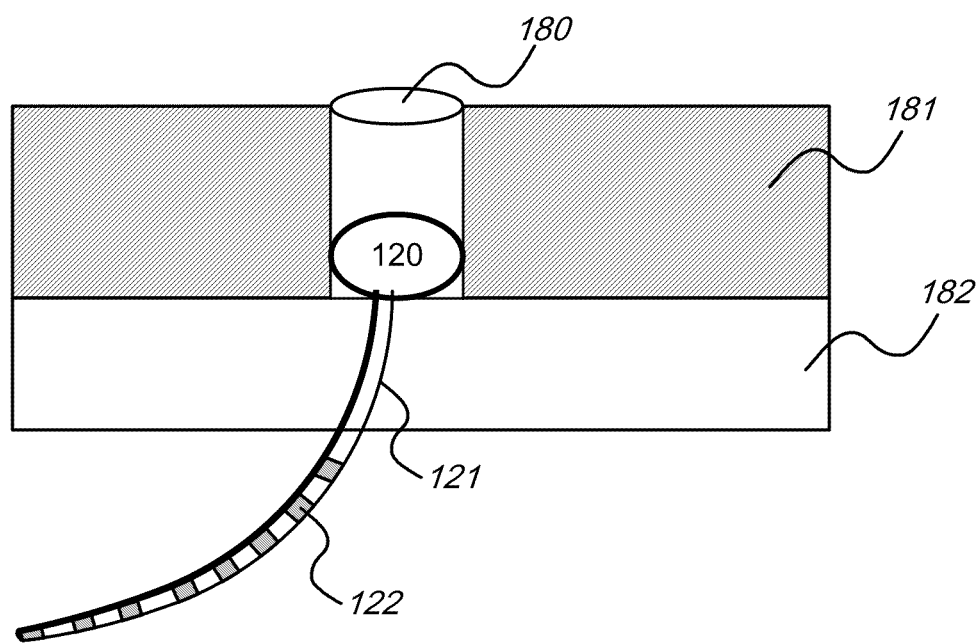

To illustrate, FIGS. 7-8 illustrate exemplary configurations wherein one or more electrodes 122 coupled to an implantable stimulator 120 are in communication with one or more stimulation sites within the brain. The configurations shown in FIGS. 7-8 are merely illustrative of the many different implant configurations that may be used in accordance with the systems and methods described herein.

For example, as shown in FIG. 7, the stimulator 120 may be implanted beneath the scalp, such as in a surgically-created shallow depression or opening in the skull. The surgically-created shallow depression or opening may be located in the parietal bone 171, the temporal bone 172, and/or the frontal bone 173. In some examples, the stimulator 120 is configured to conform to the profile of surrounding tissue(s) and/or bone(s). This may minimize pressure applied to the skin or scalp, which pressure may result in skin erosion or infection.

As shown in FIG. 7, first and second leads 121-1 and 121-2, respectively, may be coupled to the stimulator 120. In some examples, the first lead 121-1 includes one or more electrodes 122-1 disposed thereon that are configured to apply electrical stimulation to one or more stimulation sites within the brain. The second lead 121-2 may include one or more electrodes 122-2 disposed thereon that are configured to monitor for the occurrence of a seizure by sensing electrical activity of the brain. As shown in FIG. 7, the stimulating electrodes 122-1 and the sensing electrodes 122-2 may be implanted in distinct areas of the brain. It will be recognized that any number of leads 121 may be coupled to the stimulator 120 and implanted at any suitable location within the brain. It will also be recognized that each lead 121 may include any combination of stimulating and sensing electrodes.

Alternatively, as shown in the cross-sectional view of FIG. 8, the stimulator 120 may be implanted within the lumen of a hole 180 created in the skull 181 and configured to apply a stimulus at a stimulation site within the brain. The hole 180 may be a burr hole, for example, and may be created with a surgical drill or any other suitable device. The hole 180 extends at least partially into the skull 181, and, as shown in FIG. 8, may extend all the way through the skull 181 until the hole 180 is in communication with the outermost layer 182 of the brain. The stimulator 120 is placed within the lumen of the hole 180 and coupled to the walls of the hole 180 and/or the top surface of the outermost layer 182 of the brain using an adhesive, suture, or any other fastening device. Once the stimulator 120 has been implanted, the hole 180 may be covered by an appropriately sized cap (not shown).

As shown in FIG. 8, a lead 121 may be coupled to the stimulator 120 with the distal end of the lead 121 being routed to a particular location in communication with a stimulation site within the brain. A distal portion of the lead 121 may include one or more electrodes 122 configured to deliver an electrical stimulation current to the stimulation site. One or more of the electrodes 122 may additionally or alternatively be configured to monitor the brain for indicators of seizures caused by brain stimulation. A catheter (not shown) may additionally or alternatively be coupled to the stimulator 120 and routed to the stimulation site so as to deliver one or more drugs at the stimulation site.

In some alternative examples, a distal portion of the lead 121 may be placed within the brain through a burr hole created within the skull. A proximal portion of the lead 121 may exit the burr hole and be routed to an implant site of the stimulator 120 (e.g., a subcutaneous pocket made within the chest).

The preceding description has been presented only to illustrate and describe embodiments of the invention. It is not intended to be exhaustive or to limit the invention to any precise form disclosed. Many modifications and variations are possible in light of the above teaching.

What is claimed is:

1. A method of treating a patient having a medical condition, comprising:
    applying at least one stimulus to a stimulation site within the brain of the patient in accordance with one or more stimulation parameters, thereby treating the medical condition;
    detecting an event indicative of one of an impending seizure caused by the at least one stimulus before the seizure actually occurs and an actual seizure caused by the at least one stimulus; and
    applying an asynchronous electrical stimulation pattern to a location of the brain to prevent the actual seizure from occurring or to treat the actual seizure.

2. The method of claim 1, wherein the event is indicative of the impending seizure, and the asynchronous electrical stimulation pattern is applied to the location of the brain to prevent the actual seizure from occurring.

3. The method of claim 1, wherein the event is indicative of the actual seizure, and the asynchronous electrical stimulation pattern is applied to the location of the brain to treat the actual seizure.

4. The method of claim 1, wherein the event indicative of the impending seizure or the actual seizure is a brain wave having a synchronous pattern.

5. The method of claim 1, wherein the at least one stimulus comprises a synchronous electrical stimulation pattern, and wherein applying the asynchronous electrical stimulation pattern comprises switching from the synchronous electrical stimulation pattern to the asynchronous electrical stimulation pattern.

6. The method of claim 1, further comprising warning the patient of the detection of the event indicative of the impending seizure or the actual seizure.

7. The method of claim 1, wherein the at least one stimulus comprises at least one of an electrical stimulus and an infusion of one or more drugs.

8. The method of claim 1, further comprising implanting a stimulator within the patient, wherein the at least one stimulus is generated by the stimulator.

9. The method of claim 8, wherein the asynchronous electrical stimulation pattern is generated by the stimulator.

* * * * *